(12) United States Patent
Martin et al.

(10) Patent No.: US 6,805,672 B2
(45) Date of Patent: Oct. 19, 2004

(54) BLOOD FLOW MONITOR FOR SHOCK AND RESUSCITATION

(75) Inventors: Gregory T. Martin, Cambridge, MA (US); Harry Frederick Bowman, Needham, MA (US)

(73) Assignee: Thermal Technologies, Inc., Cambridge, MA (US)

(*) Notice: Subject to any disclaimer, the term of this patent is extended or adjusted under 35 U.S.C. 154(b) by 210 days.

(21) Appl. No.: 10/147,013

(22) Filed: May 16, 2002

(65) Prior Publication Data

US 2002/0173731 A1 Nov. 21, 2002

Related U.S. Application Data

(60) Provisional application No. 60/291,698, filed on May 17, 2001.

(51) Int. Cl.[7] .................................. A61B 5/02
(52) U.S. Cl. ...................... 600/504; 600/549
(58) Field of Search ................ 600/549, 555, 600/587, 593, 481, 504

(56) References Cited

U.S. PATENT DOCUMENTS

| | | |
|---|---|---|
| 3,359,974 A | 12/1967 | Khalil |
| 4,059,982 A | 11/1977 | Bowman .................... 73/15 A |
| 4,217,910 A | 8/1980 | Khalil |
| 4,741,343 A | 5/1988 | Bowman et al. |
| 4,859,078 A * | 8/1989 | Bowman et al. ............ 600/549 |
| 5,009,234 A | 4/1991 | Alt |
| 5,692,514 A | 12/1997 | Bowman |
| 5,797,398 A | 8/1998 | Bowman |
| 5,863,291 A | 1/1999 | Schaer |
| 6,064,914 A | 5/2000 | Trachtenberg |
| 6,165,132 A | 12/2000 | Bowman .................... 600/505 |
| 6,203,501 B1 | 3/2001 | Bowman |
| 6,258,046 B1 * | 7/2001 | Kimball et al. ............. 600/593 |

FOREIGN PATENT DOCUMENTS

| | | |
|---|---|---|
| FR | 2.112.767 | 6/1972 |
| WO | WO 91/17703 | 11/1991 |
| WO | WO 95/05115 | 2/1995 |

* cited by examiner

Primary Examiner—Eric F. Winakur

(57) ABSTRACT

A shock monitor comprising one or more probes, for measuring physiological conditions indicative of shock, and a controller for calculating blood flow values, as an indicator of the state-of-shock, is disclosed. The probe is used to introduce an input signal and produces an output signal, which represents the state-of-shock of the tissue in communication with the probe. The output signal is used to calculate a blood flow value.

20 Claims, 12 Drawing Sheets

BLOOD FLOW MONITOR FOR SHOCK AND RESUSCITATION

DOMESTIC PRIORITY CLAIM

This application claims domestic priority from U.S. Provisional Application Ser. No. 60/291,698, filed May 17, 2001, now abandoned, the disclosure of which is hereby incorporated herein by reference.

FIELD OF THE INVENTION

The invention relates to monitoring physiological conditions as an indicator of shock. More specifically, the invention relates to monitoring of blood flow in tissues as an indicator of shock.

BACKGROUND OF THE INVENTION

Shock is a clinical syndrome in which blood flow to the capillary beds (the perfusion) is decreased. Shock occurs in about 1 million patients/year in the United States and a total of about 3 million patients/year are at risk. Shock occurs when arterial pressure and subsequently tissue blood flow drop so low that the amount of delivered oxygen is inadequate to meet the metabolic needs of the tissue.

During shock, the body directs blood to the heart and the brain, often at the expense of "sacrificial" organs such as the liver, skin, muscle, and gut. Prolonged shock may diminish blood flow to the gut such that the normal intestinal barrier function is disrupted and gut-derived bacteria and endotoxins are translocated to other organs via the blood. This, in turn, may lead to bacteremia, sepsis, inflammatory response and ultimately multi-organ failure—one of the major causes of patient mortality.

Conventional therapy for shock involves resuscitation. Resuscitation therapy is directed toward first assuring that oxygen is being supplied to the patient and that it is being transported through the circulation to the organs to support life. Circulatory distress is addressed with the infusion of fluids and pharmacological agents (inotropes) to increase cardiac output. Therapy is typically titrated to attain a target heart rate (HR), systolic blood pressure (BP), mean arterial blood pressure (MAP), urine output, and normal arterial pH. Cardiac output (CO) may also be monitored. While these conventional parameters are thought to give an indirect indication of tissue oxygenation, they correlate poorly with survival in critically ill patients (Astiz and Rackow, 1993; Shoemaker et al., 1993).

While the global, systemic parameters (HR, BP, CO, etc.) are readily accessible, these non-specific variables cannot tell if oxygen deprivation is occurring in one or more tissue beds or organs. Given the limitations of global monitoring, a number of local tissue monitoring techniques have been proposed to detect the onset of shock and provide an optimal "end point" to guide therapy for complete resuscitation. Techniques have been proposed to monitor parameters ($pO_2$, pH, $pCO_2$, lactate levels, etc.) in sacrificial tissues that are susceptible to hypoperfusion, hypoxia and ischemia to provide an optimal "end point" to guide resuscitation therapy. While these parameters are an attempt to assess the local tissue blood flow, and hence the oxygen delivery, these parameters also depend on metabolism and their respective arterial blood concentrations. Since during shock the blood supply is directed to the heart and the brain, often at the expense of the liver, skin, muscle and gut, these "sacrificial" organs are thought to provide sites to monitor shock onset and resuscitation end points. The sacrificial organs are the first to develop hypoperfusion at shock onset and are the last to be restored after resuscitation. These prior methods, however, have not revealed an effective correlation between patient survival and outcome and are not well suited for rapid and simple use in a clinical setting. Therefore, a reliable monitor for gut ischemia is needed, because such measurements could significantly impact the management of shock patients.

INFORMATION DISCLSOURE

The following patents are cited as background information herein, and to the extent necessary for a full and complete understanding of this invention, these patents are hereby incorporated herein by reference: U.S. Pat. Nos. 4,059,982, 4,852,027, 6,2221,025, 6,010,455, 5,792,070, 5,771,261, 5,769,784, 5,404,881, 5,335,669, 5,205,293, 4,859,078, 4,413,633, 4,392,005, 4,306,569, 3,818,895, 3,623,473 and Design Pat. No. 384,412.

SUMMARY OF THE INVENTION

An object of the present invention is to provide a shock monitoring apparatus. It is a particular object of certain aspects to use the shock monitoring apparatus to monitor for shock through measurement of rectal wall blood flow as a proxy for gut ischemia.

In accordance with a first aspect, a shock monitoring apparatus comprises a probe and a controller. Optionally, the apparatus comprises one or more additional probes or sensors. The probe typically functions to provide an input stimulus to an area of interest, such as to tissue in the rectum. That is, the probe transmits an input signal, e.g., heat, into the tissue region contacted by the probe. The input signal functions to perturb the tissue. The tissue functionally responds to such perturbations, and this functional response can be correlated with the physiological state of the tissue, e.g., low blood flow to the tissue, etc., as an indicator of the state-of-shock (SOS) in the patient. In certain embodiments, a reference probe is used to account for baseline fluctuations in the tissue temperature. The system measures the functional response of the tissue and transmits an output signal to a controller. The controller then typically performs one or more operations on the signal, e.g., recording, adding, subtracting, comparing, etc. In certain embodiments described here, the output signal is compared with tabulated values contained in the controller to calculate a blood flow value based on known blood flow values.

In accordance with preferred embodiments, a system for monitoring shock comprises an apparatus for supplying heat to tissue and measuring the thermal response in the tissue, which is functionally related to physiological conditions in the tissue, e.g., blood flow in the tissue, and an device for calculating a blood flow value. Optionally, the system comprises one or more additional probes or other sensors. Such apparatus for supplying heat to tissue are well known to those skilled in the art and include, but are not limited to thermistors, thermocouples, electric wires, etc.

In accordance with additional aspects, the heating apparatus may be electrically energized, or magnetically energized as the case may be, to elevate the temperature of the apparatus and/or the probe. In preferred embodiments, the heating apparatus is designed such that only the portion of the probe in contact with the tissue is heated.

The blood flow values may be representative of several indicators of shock including but not limited to blood flow in tissue, oxygen levels in the tissue, in pH, etc. In certain embodiments, the blood flow values are converted to State- Of-Shock (SOS) values to facilitate rapid clinical assessment of a patient's condition. For example, if blood flow value is between 95–100% of non-shock blood flow value, e.g. the blood flow value in the absence of shock, an SOS value of "1" may be assigned. If the blood flow is between 85–95% an SOS value of "2" may be assigned and so on. It is preferred, but not required, that the SOS values are on a scale of "1–5", where an SOS value of "1" represents little or no shock and an SOS value of "5" represents severe shock. One skilled in the art will recognize that the scaling of blood flow values is not limited to the "1–5" scale or that the percentages of the blood flow values necessarily are limited to the scaling described here.

In accordance with a method aspect, the shock monitoring apparatus is used to input a stimulus into the tissue, measure the response of the tissue to the stimulus, transmit and record the response of the tissue in an output signal, and output or display the results of the measurement for evaluation of the patient's physiological state. The stimulus may comprise heat, an electric current, a voltage, or any other signal capable of perturbing a physiological condition indicative of blood flow, e.g., the temperature, of the tissue. The response of the tissue is typically measured using the probe itself. In other embodiments, the response of the tissue is measured using any of the sensors well known to those skilled in the art, such as those manufactured by Thermal Technologies Inc (Cambridge, Mass.) and Diametrics Medical, Inc. (St. Paul, Minn.).

The output signal typically represents a value functionally related to the response of the tissue to the input signal. For example, the output signal may reflect an amount of heat required to elevate the temperature of the tissue by a certain quantity, the amount of current required to elevate the temperature of the tissue by a certain quantity, the amount of power required to elevate the temperature of the tissue by a certain quantity, the amount of heat transferred from the probe to the tissue or from the tissue to the probe, the intrinsic thermal conductivity of the tissue, perfusion values, the amount of heat required to maintain a constant temperature, etc.

In accordance with preferred embodiments, the temperature of a heating apparatus, in contact with tissue, is elevated above the baseline temperature of the tissue. Such heating typically is performed by introduction of an electric current, e.g., an electrical signal, into an electric heater in contact with the tissue. An electrical signal is produced that is indicative of the amount of energy required to raise the temperature of the heating apparatus and the rate at which the heat from the apparatus is transferred to the tissue. Based on the values obtained, a blood flow value can be calculated. Without wishing to be bound by any scientific theory, a value indicative of shock may be the difference between a blood flow signal indicative of no shock and the signal from the current state of the tissue, e.g., a difference of zero would be representative of no shock. Therefore, relative changes in the blood flow value can be monitored as an indicator of functional changes in the tissue. After measurement of the output signal, the temperature of the heating apparatus is then lowered back to the baseline temperature of the tissue. The steps of elevating the temperature, recording the signal, and reducing the temperature to baseline are repeated continuously (or cyclically with an optional delay between cycles) to provide for online monitoring of a patient's blood flow values. Reductions in the blood flow values from a base condition, e.g., blood flow values in the absence of shock, are indicative of the likelihood of the occurrence of shock. Therefore, changes in a patient's blood flow values, during continuous monitoring of the patient, can allow physicians to undertake measures to prevent the onset of shock or to reduce the pathological and physiological damage that would occur in the absence of any intervention.

In accordance with preferred embodiments, the shock monitoring apparatus may be used to iteratively calculate blood flow values. Such systems typically comprise a probe in contact with tissue, e.g., a thermistor, a controller for introducing an input signal into the probe to perturb the tissue, e.g., a controller to cause the temperature of the thermistor to cyclically rise and fall, the rate of temperature rise in an initial time period within each energizing and deenergizing cycle is substantially a function of the intrinsic thermal conductivity of tissue in thermal contact with the thermistor. The controller also may transmit an output signal that can be used to iteratively calculate values for determining the blood flow value of the tissue. Such calculations may be performed using the controller itself or using an external calculating device such as a computer. Numerous calculations and operations may be performed on the output signal. In accordance with preferred embodiments, the output signal is used to calculate an intrinsic thermal conductivity. Without wishing to be bound by any scientific theory, the intrinsic thermal conductivity typically is represented by the temperature rise in an initial time interval. This intrinsic thermal conductivity is a function of the power provided to the probe to raise its temperature to a predetermined value, since more power typically introduces more heat. The intrinsic conductivity value is used to calculate a blood flow (perfusion) value indicative of shock.

In accordance with preferred embodiments, the calculated blood flow value (perfusion value) can be used to recalculate the calculated value of thermal conductivity. The recalculated conductivity value is used to recalculate the calculated value of the blood flow (perfusion). Such steps of calculating thermal conductivity, calculating blood flow values, recalculating thermal conductivity and recalculating blood flow values are typically repeated until the value for blood flow does not change substantially. That is, the iterative calculation can be performed until the perfusion values do not change by more than about 5%, preferably no more than about 1%, and most preferably no more than about 0.1%. For example, the calculation stops when successive thermal conductivity values and blood flow values differ by less than about 0.05%. Such values are referred to here as substantially converged blood flow values. After calculating the substantially converged blood flow values, an SOS value may be calculated and used as an indicator of shock. The calculated blood flow values (or SOS values) may be displayed or recorded for monitoring of a patient's susceptibility to shock. The changes and variations in such values can be correlated with the likelihood of shock. Automated monitoring systems may be designed that alert clinical personnel when a patient's SOS values are outside an acceptable range of SOS values. Thus, systems comprising the shock-monitoring device described here provide for continuous and automated monitoring of patient's in a clinical setting.

The shock monitoring apparatus (and systems comprising the shock monitoring apparatus) disclosed here provides medical facilities the ability to monitor patients for the probability of shock onset. Such devices can aid in reduction of the mortality rate from shock and can also be used as an additional monitoring technique to assess the clinical status of patients.

Certain especially preferred aspects of the present invention may be summarized as follows:

One aspect of the present invention is directed to a system for monitoring shock comprising:

means for supplying heat to tissue in the inner wall of the rectum;

means for sensing in the tissue a thermal response functionally related to the perfusion of blood in the tissue; and means for calculating a value indicative of shock as a function said thermal response. Preferably, the means for supplying heat to tissue comprises a thermistor. Advantageously, the sensor comprises a thermal diffusion probe. Alternatively, the sensor comprises an intraluminal probe.

Another preferred aspect of the present invention is directed to a shock monitor comprising:

a thermistor for thermal contact with tissue at a site on the inner wall of the rectum;

means for electrically energizing said thermistor to elevate the temperature of said thermistor above the baseline temperature of tissue at said site;

means for producing an electrical signal having a value functionally related to the electrical energy supplied to said thermistor and the rate at which heat from said thermistor is transferred in said tissue;

means for producing a signal indicative of shock as a function of said electrical signal.

Another preferred aspect of the present invention is directed to a shock monitor comprising:

thermistor means for thermally contacting living tissue at a site on the inner wall of the rectum;

means for electrically energizing and deenergizing said thermistor means cyclically to cause the temperature of said tissue to rise and fall cyclically;

means for producing a signal functionally related to the power used to energize said thermistor during each energizing and deenergizing cycle;

means responsive to the power related signal from said producing means for producing a signal during each energizing and deenergizing cycle as a function of perfusion in said tissue; and means for computing a value for blood flow in said tissue indicative of shock during each energizing and deenergizing cycle as a function of the perfusion related signal. Preferably, the means for computing a value comprises a microprocessor. Advantageously, the means for computing a value comprises an embedded microdevice.

Another preferred aspect of the present invention is directed to a system for producing a signal indicative of shock comprising:

a thermistor for contacting the inner wall of the rectum to establish thermal contact with tissue at a site in the inner wall of the rectum;

control means for electrically energizing and deenergizing said thermistor cyclically to cause the temperature of said thermistor to cyclically rise and fall, the rate of temperature rise in an initial time period within each energizing and deenergizing cycle being substantially a function of the intrinsic thermal conductivity of tissue in thermal contact with said thermistor;

means for producing a signal functionally related to the power used to energize said thermistor during each energizing and deenergizing cycle; and iterative calculating means for:

calculating intrinsic thermal conductivity in the initial time interval during each energizing and deenergizing cycle as a function of the temperature rise in the initial time interval and the power related signal produced by said producing means;

calculating perfusion in a subsequent time interval during each energizing and deenergizing cycle as a function of the calculated value of intrinsic thermal conductivity;

recalculating intrinsic thermal conductivity in the first time interval using the calculated value of perfusion;

recalculating perfusion in the subsequent time interval using the recalculated value of intrinsic thermal conductivity; and recalculating values for intrinsic thermal conductivity and perfusion, in alternating fashion, until the recalculated values of perfusion converge to a substantially unchanging value, using in each recalculation of perfusion the previously recalculated value of intrinsic thermal conductivity and in each recalculation of intrinsic thermal conductivity the previously recalculated value of perfusion.

Another preferred aspect of the present invention is directed to a method of monitoring shock in a living subject comprising the steps of:

supplying heat to tissue in the inner wall of the rectum;

sensing in the tissue a thermal response functionally related to the perfusion of blood in the tissue; and calculating a blood flow value indicative of shock as a function said thermal response. Preferably, the heat is supplied using a thermistor. Advantageously, the blood flow value is calculated by comparing the thermal response with a table of thermal response values.

Another preferred aspect of the present invention is directed to a method of monitoring shock comprising the steps of:

contacting the inner wall of the rectum with electrically energizable thermistor means to establish a heat transfer path between said thermistor means and tissue at a site along the inner wall of the rectum;

energizing said thermistor means to elevate the temperature of said thermistor means above the baseline temperature of said tissue;

sensing the thermal response in said tissue to the application of heat from said thermistor means; and calculating a blood flow value indicative of shock as a function of the thermal response in said tissue sensed in said sensing step. Preferably, the blood flow value is calculated by comparing the thermal response with a table of thermal response values. Advantageously, said calculating step comprises the steps of:

calculating intrinsic thermal conductivity in a first time interval during said energizing step;

calculating perfusion in a subsequent time interval during said energizing step using the calculated value of intrinsic thermal conductivity;

recalculating values for intrinsic thermal conductivity and perfusion in alternating fashion, until the recalculated values of perfusion converge to a substantially unchanging value, using in each recalculation of perfusion the previously calculated value of intrinsic thermal conductivity and in each recalculation of intrinsic thermal conductivity the previously calculated value of perfusion; and calculating a blood flow value indicative of shock as a function of the converged value of perfusion.

Another preferred aspect of the present invention is directed to a method of monitoring shock comprising the steps of:

contacting the inner wall of the rectum with a thermistor to establish a thermal transfer path with tissue at a site in the inner wall of the rectum;

electrically energizing and deenergizing said thermistor cyclically to cause the temperature of tissue in thermal contact with said thermistor to cyclically rise and fall, the rate of temperature rise in an initial time period within each energizing and deenergizing cycle being substantially a function of the intrinsic thermal conductivity of tissue in thermal contact with said thermistor;

producing a signal functionally related to the power used to energize said thermistor during each energizing and deenergizing cycle;

calculating intrinsic thermal conductivity of tissue at said site in an initial time interval during each energizing and deenergizing cycle as a function of the temperature rise and said power related signal in the energizing and deenergizing cycle;

calculating perfusion in a subsequent time interval during each energizing and deenergizing cycle as a function of the calculated value of intrinsic thermal conductivity;

recalculating intrinsic thermal conductivity in said first time interval using the calculated value of perfusion;

recalculating perfusion in said subsequent time interval using the recalculated value of intrinsic thermal conductivity;

recalculating values for intrinsic thermal conductivity and perfusion, in alternating fashion, until the recalculated values of perfusion converge to a substantially unchanging value, using in each recalculation of perfusion the previously recalculated value of intrinsic thermal conductivity and in each recalculation of intrinsic thermal conductivity the previously recalculated value of perfusion; and processing said substantially unchanging perfusion value during each energizing and deenergizing cycle to provide a blood flow signal indicative of shock.

Another preferred aspect of the present invention is directed to a system for producing a signal indicative of shock comprising:

thermistor means for thermally contacting living tissue;

means for electrically energizing and deenergizing said thermistor means cyclically to cause the temperature of said tissue to rise and fall cyclically;

means for producing a signal functionally related to the power used to energize said thermistor during each energizing and deenergizing cycle; and means responsive to the power related signal from said producing means for producing a signal indicative of shock during each energizing and deenergizing cycle. Preferably, the system further comprises a blood flow model wherein said signal indicative of shock is a function of the relationship of said power related signal to said blood flow model. Advantageously the system further comprises a model that relates temperature and power to tissue blood flow wherein said signal indicative of shock is a function of the relationship of said power related signal and the change in temperature produced by said energizing and deenergizing means to a blood flow value determined by said model. In addition, the system will utilize the relationship of said power related signal and the change in temperature produced by said energizing and deenergizing means is the ratio of said power related signal to said change in temperature. In such systems the thermistor means may comprise means for thermally contacting a site on the inner wall of the rectum.

DETAILED DESCIPTION OF THE PREFERRED EMBODIMENTS

Figure 1:
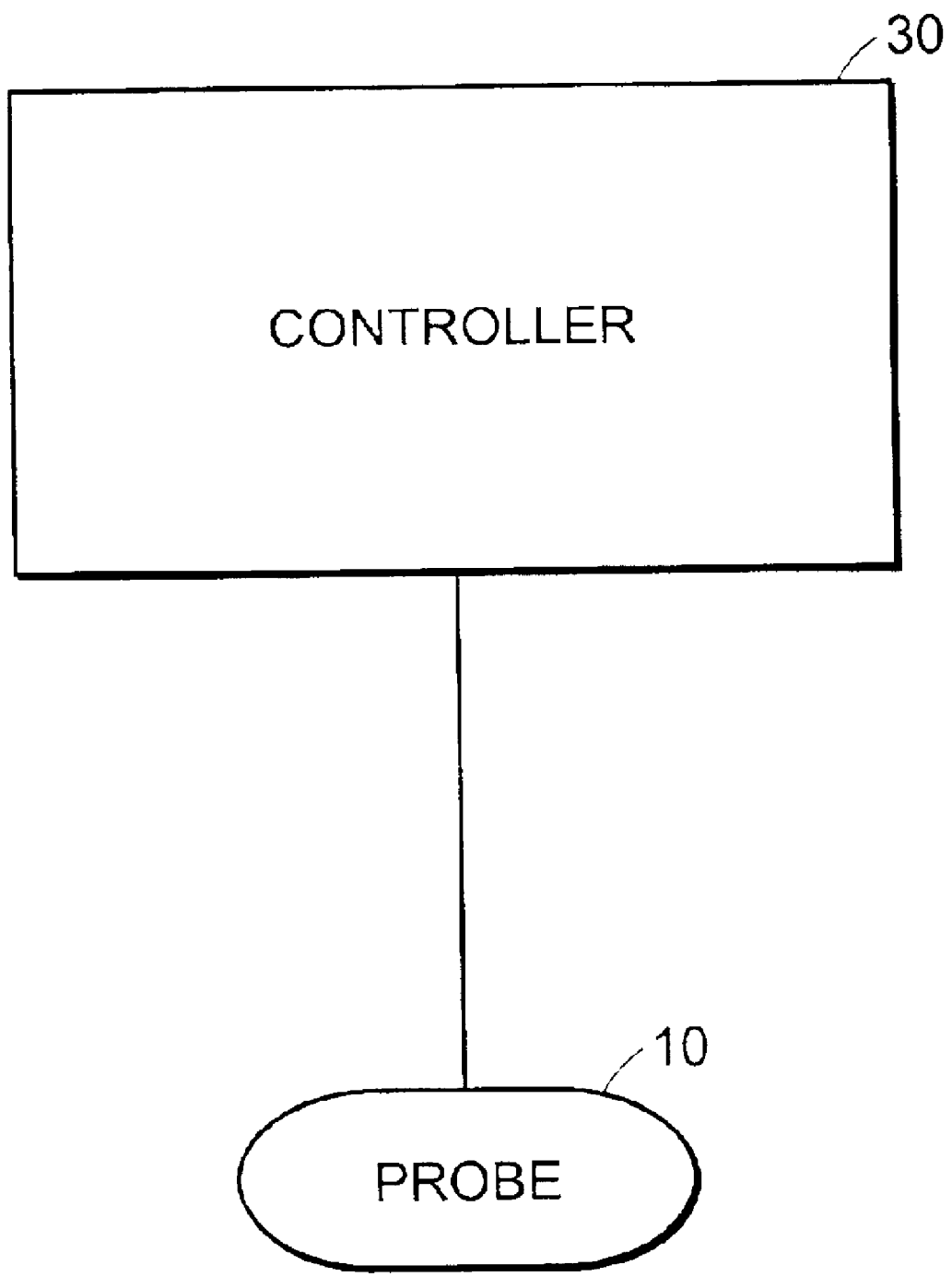
FIG. 1 shows a system for monitoring shock in accordance with a first embodiment.

It will be recognized from the above, that the shock monitoring apparatus disclosed here can be assembled and formed using innumerable probes, sensors, and controllers. The precise sizes, configurations and types of probes sensors and controllers, including the choice of materials and properties of the probes and sensors, design of the shock monitoring apparatus, and the like will depend in large part on the particular application for which it is intended. For convenience in this more detailed description of certain preferred embodiments, the shock monitoring apparatus will generally be of a type suitable for use in monitoring and measurement of physiological conditions in the inner rectal wall. It will be within the ability of those skilled in the art, however, given the benefit of this disclosure, to select suitable materials and designs, as well as manufacturing techniques, for production and use of shock-monitoring devices in accordance with the principles of the present invention, suitable for these and other types of applications.

Certain preferred embodiments of the shock monitoring apparatus disclosed here comprise a probe for contacting and heating tissue, a control device for measuring the response of the tissue, and a controller for recording, calculating, and outputting any signals received from the measuring device. Optionally, the apparatus comprises one or more additional probes or sensors. The probe is typically introduced into a patient using any of the standard techniques known to those skilled in the art for introducing catheters, laparoscopes, etc.

In certain embodiments, an introduction device is used to facilitate introduction of the probe, e.g., insertion of a sheath or hollow tube into the rectum to facilitate introduction of the probe through the sheath and into the rectum. The probe, or the body of the probe as the case may be, preferably comprises materials that are capable of long-term implantation in the body and preferably do not elicit any immune response or any adverse local response from surrounding tissue. Suitable bio-compatible materials are well known to those skilled in the art and include but are not limited to Teflon, polyvinylprolidone, polyethylene glycol, or other materials which are non-immunogenic or hypo-allergenic.

The probe may comprise innumerable apparatus for introducing perturbations or signals into tissue or organs in contact with the probe. Such apparatus include but are not limited to thermistors or klystrons for introduction of heat, magnetic coils for introduction of magnetic fields, electrodes for introduction or measurement of local currents, devices for introduction of ultrasonic forces and the like. An input signal typically is conveyed by one or more wires or leads in communication with the probe. The input signal may induce heating of the probe, as in the case of a thermistor, generation of a magnetic field, as in the case of magnetic coils, etc. The result of the input signal, e.g., increase in local temperature, is typically used to perturb the tissue in contact with the probe. Certain preferred embodiments are directed to the use of a non-invasive probe having thereon a thermistor to which power is applied to heat the thermistor and, accordingly, to heat the tissue contacting the thermistor. Other embodiments, including invasive embodiments, are possible and will be readily recognized by those skilled in the art given the benefit of this disclosure.

Examples of probes that are adapted for non-invasive use are shown in U.S. Pat. No. 4,859,078, the entire disclosure of which is hereby incorporated herein by reference. Probes such as these can be used on the skin surface or, during surgery, on the surface of an internal organ without penetrating the skin or organ with the probe. The volume of tissue within the measurement field is that volume of tissue that is heated above the tissue baseline temperature. While not wishing to be bound by any scientific theory, it is currently believed that the functional response of the tissue, in response to the signal introduced by the probe, reflects the state-of-shock of the tissue. One skilled in the art given the benefit of this disclosure will be able to select suitable probes for introducing an input signal into tissue depending on the intended use of the shock monitoring apparatus.

The heaters of the shock monitoring system are typically located proximal to the probe and/or within the same housing as the probe. That is introduction of the probe to the tissue, e.g., the inner wall of the rectum, typically also introduces the heater. In certain embodiments, the heater and the probe are the same apparatus. For example, in embodiments where the probe comprises a thermistor, the thermistor is energized to heat the subject tissue. The power required to heat the thermistor provides a measure of the thermal response of the tissue, e.g., a thermal response functionally related to the perfusion of blood in the tissue (suitable devices for separately measuring this thermal response are well known to those skilled in the art and include but are not limited to thermometers, thermocouples, additional thermistors, and the like). The power signal may be produced by one or more electrical components or circuits for converting the measured thermal response into a desired signal, such as a current, voltage, etc. One skilled in the art given the benefit of this disclosure will be able to select and design suitable probes, heaters, and/or sensors for introducing power signals into the probe and for measuring the functional responses of tissues in response to an introduced signal.

The signal or signals are transmitted to a controller. Such transmission typically occurs through wire communication between the probe and the controller. In other embodiments, the transmission from the probe to the controller occurs Tirelessly using standard wireless communication methods, such as IEEE 802.11 b protocols, hardware, and the like, known to those skilled in the art. The controller may comprise one or more devices for collecting the signals received from the probe. Additionally, the controller typically is capable of performing one or more mathematical operations on the received signals and is capable of storing the signals. Preferably, the controller comprises an interface for the probe, e.g., a RS-232 interface or other comparable interface, a microprocessor, a readable/writeable memory, and one or more devices for storing data, e.g., a floppy disk, hard drive, or other magnetic or optical media.

In accordance with preferred embodiments, a system for monitoring shock comprises a thermal probe 10 that thermally communicates with tissue in contact with the probe 10 (See FIG. 1). The probe is in electrical communication with a controller 30. In certain embodiments, the probe incorporates an embedded thermistor, e.g. a distal thermistor is embedded in the tip of a narrow gage catheter (1-mm diameter). The catheter is inserted into thermal contact with the inner wall of the rectum, and effects thermal contact with the tissue. The thermistor, adapted for thermal contact with the tissue, is heated to a small increment above the tissue temperature baseline. (For example the temperature of the thermistor surface may be elevated to a predetermined temperature approximately 2–5° C. above the tissue temperature baseline.) A second probe, a reference probe or thermistor, may be embedded in the catheter for monitoring tissue baseline temperature and compensating for baseline temperature fluctuations. The distal thermistor is heated at intervals by a power source within the controller that is electrical communication with the thermistor. The power required to elevate the temperature in an interval is indicative of a value of a selected thermal characteristic, for example, thermal conductivity and/or thermal diffusivity, in tissue at the location of the thermistor. The power used results in an output signal from the power source functionally related to the thermal response in the tissue to the application of heat. The output signal typically is used to calculate a value indicative of thermal conductivity and/or blood flow at the site of the probe.

While not wishing to be bound by any scientific theory, when a thermistor is in thermal communication with live tissue at a site where blood flow is to be assessed, the power dissipated by the heated thermistor (typically within the range of 0.005–0.01 W) provides a measure of the ability of the tissue to carry heat by both conduction in the tissue and convection due to tissue blood flow. In operation, the thermistor is energized and a thermal field propagates into tissue contacting and surrounding the thermistor. The initial propagation of the field is due substantially to inherent tissue conductivity (thermal conductance). Subsequent propagation of the field is affected more by tissue convection (blood flow or perfusion). A controller, e.g., a monitor or data processor, controls the probe, records the data and distinguishes between the effect of the inherent thermal conductivity characteristic of the tissue and convective heat transfer due to tissue blood flow. The inherent or intrinsic thermal conductivity of the tissue at the site of the thermistor is determined from the initial rate of propagation of the thermal field in the tissue, separated from the effects of convective heat transfer.

In certain embodiments, the signals received by the controller are processed using one or more data processing functions, e.g., a microprocessor and an algorithm, to distinguish and separate the thermal conductive effects of the heated thermistor. The temperature change produced in the tissue is permitted to vary in any arbitrarily selected manner with time. The power required to heat the tissue and the resulting temperature change are recorded. An intrinsic thermal conductivity value is calculated using data obtained at an initial time period. The conductivity value is used to assess the blood flow (perfusion) of the tissue at the site of the probe. Computation can be based on a thermal model requiring a series of heating cycles with measurements at two or more selected times within each cycle. These measurements occur during a temperature change cycle in which the temperature of tissue at the selected site is raised from a first unperturbed value to a second value and relaxed back to an unperturbed value.

In accordance with preferred embodiments, a thermal model and related mathematical equations are described in U.S. Pat. No. 4,852,027 to Bowman et al., the entire disclosure of which is hereby incorporated herein by reference. When data used to assess the tissue perfusion includes measurements made for at least two selected time periods in an overall temperature changing cycle, data processing occurs in an interactive or iterative operation so as to converge relatively rapidly to a final solution for tissue perfusion at the site of the probe. In one embodiment, the thermistor is energized to heat the tissue at the selected site from an unperturbed temperature value to a second higher temperature value and then permitted to decay, i.e. to cool, to an unperturbed value. Power is applied to energize the thermistor in any appropriate manner that produces an arbitrarily selected change as a function of time in the volume mean temperature of the tissue surrounding the thermistor. Measurements are made in at least two selected time periods during the heating and cooling cycle.

In accordance with other embodiments, when direct computation of perfusion does not lead to an acceptably accurate calculation of blood flow, an iterative process may be used to optimize the accuracy of the blood flow calculation. In the iterative computation, the temperature of the thermistor is caused to rise to initiate each heating cycle and relax at the end of each cycle. An initial determination of a value for intrinsic thermal conductivity (or thermal diffusivity), is calculated during a first time period within the initial heating cycle and each subsequent heating cycle. This first time period calculation is made at the initial stage of each heating cycle. A calculation of the convective heat transfer effect in the tissue due to blood flow or perfusion of the tissue is separately calculated at a second time period, later in the heating cycle, using the conductivity value obtained in the initial time period and perfusion data obtained at the second time period, the effects of convective heat transfer during the second time period being greater than the convective heat transfer effects during the first time period. The perfusion value obtained at the second time period is used to recalculate a second, more accurate value of thermal conductivity in the first time period. The recalculated value of conductivity is used to recalculate a second, more accurate, value of perfusion. The process can be repeated as many times as necessary. In each calculation of perfusion the value of conductivity obtained in the prior calculation is used. Similarly, in each successive computation of thermal conductivity the prior value of perfusion is used. The iterative process will lead to convergence wherein the same value of perfusion is obtained in successive calculations. This value is the blood flow value of tissue at the location of the probe. The iterative process is stopped preferably when successive values differ by no more than about 5%, preferably no more than about 1%, and more preferably no more than about 0.1%. The calculation of blood flow in the above described embodiment thus takes into account the effective thermal conductivity of the subject tissue, that being the convective heat transfer effect produced by tissue perfusion plus the intrinsic thermal conduction of the tissue, and separates the convective heat transfer effect from the intrinsic thermal conductivity.

Figure 2:
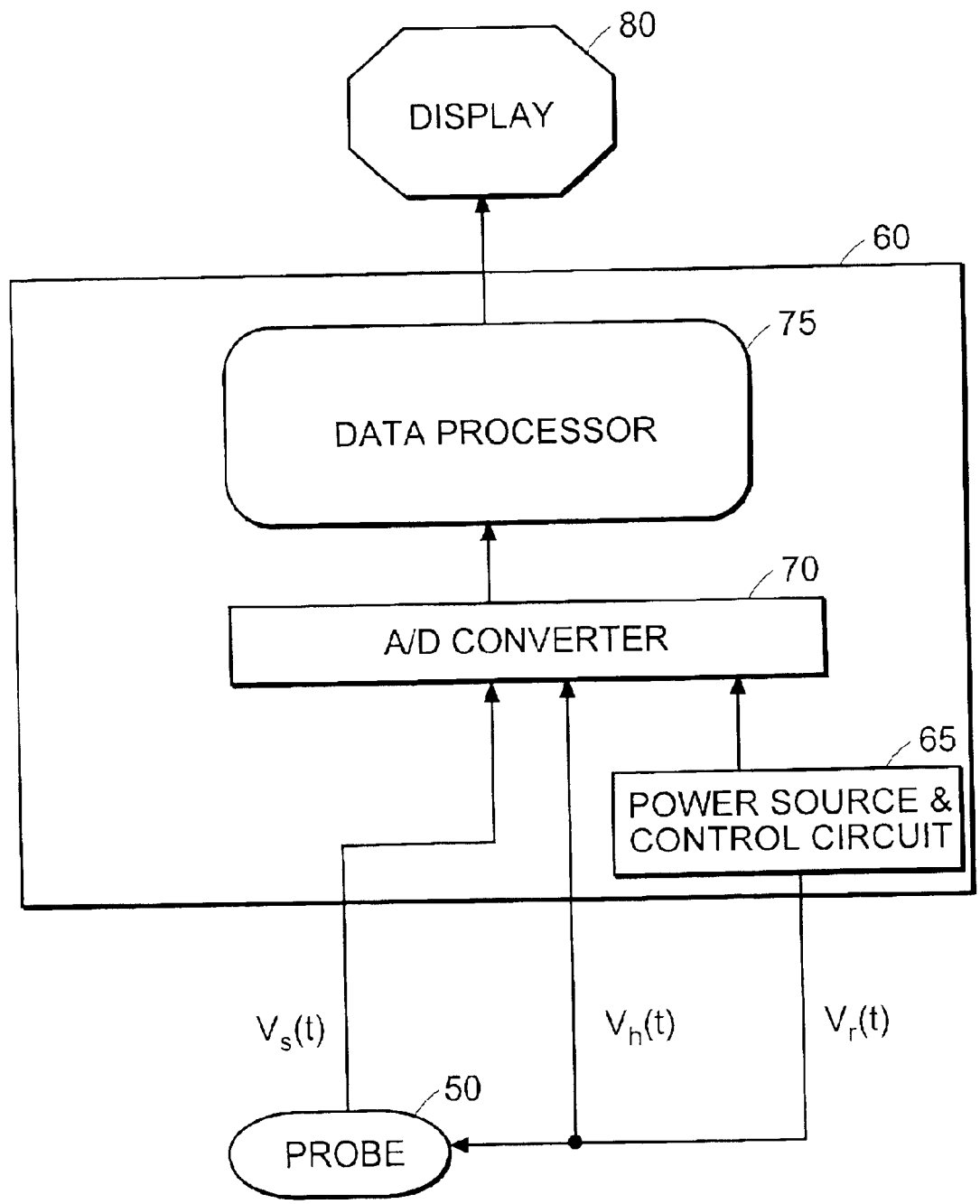
FIG. 2 shows a system for monitoring shock in accordance with a second embodiment.
Figure 3:
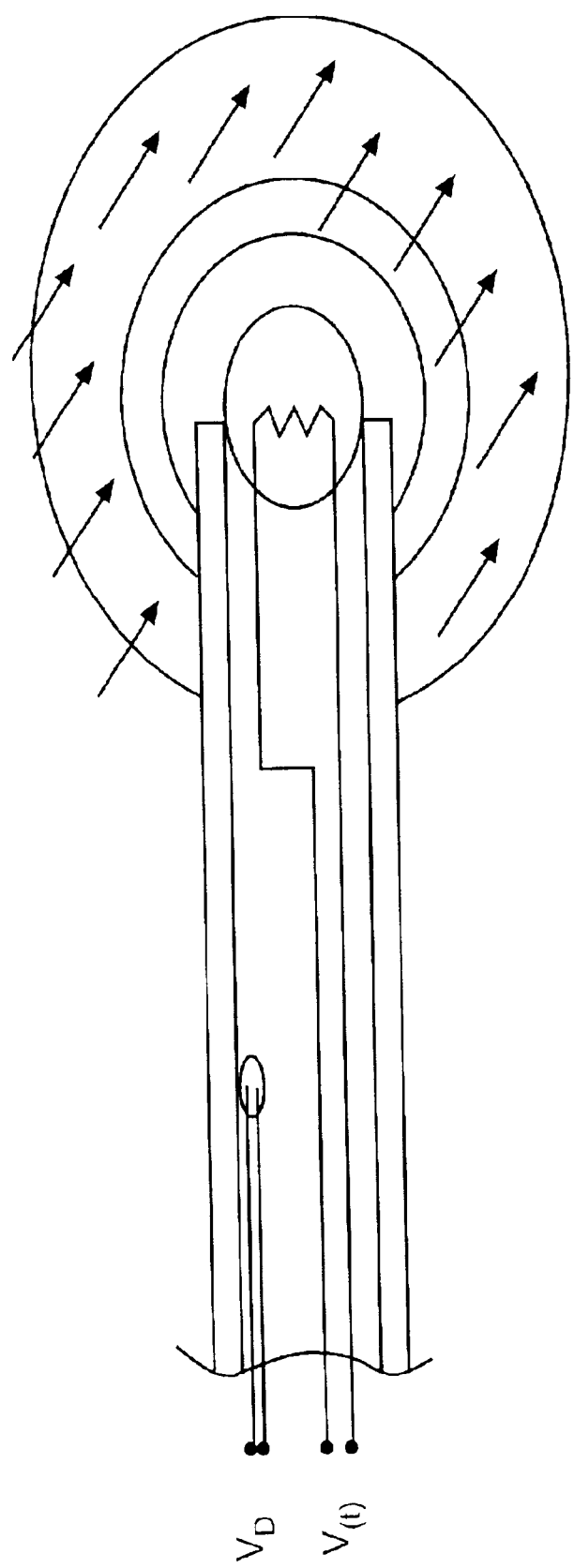
FIG. 3 shows a probe for use in a system for monitoring for shock in accordance with a first embodiment.

In accordance with preferred embodiments, a system such as that shown in FIG. 2, for example, and a probe comprising a thermistor of the type shown in FIG. 3 can be used to monitor blood flow in the inner wall of the rectum. Referring to FIG. 2, a probe 50 may be placed in communication with a tissue, such as the tissue present in the inner wall of the rectum. A self-heating distal thermistor (see FIG. 3) mounted on the probe 50 is heated by power from an electrical power source and control circuit 65 located in a controller 60 (see FIG. 2). In FIG. 2 the voltage supplied by the power source and control circuit 65 is indicated as $V_h(t)$. The probe 50 is energized to heat a surrounding volume of tissue. The mean temperature of the thermistor of the probe 50 is rapidly raised to a predetermined level above its initial equilibrium temperature, or above the baseline temperature of tissue, by the power source and control circuit 65. A typical heat distribution pattern has a Gaussian distribution centered at the mean temperature of the thermistor. The maximum temperature, thus, occurs at the center of the thermistor bead and decreases in all directions therefrom to the reference temperature; that is, it decreases to the baseline temperature of the unperturbed tissue surrounding the site of the thermistor. The volume of tissue surrounding the thermistor in which the temperature of the tissue is elevated to any substantial extent by the heated thermistor is referred to as the measurement field.

While not wishing to be bound by any scientific theory, the rate at which heat is transferred from the thermistor is a function of the effective thermal conductivity of the tissue. Therefore, the power used (or dissipated) in the thermistor to maintain a predetermined elevated temperature level is also a function of the effective thermal conductivity of the surrounding tissue. The effective thermal conductivity of living tissue has two principal components, intrinsic thermal conductivity of the tissue and tissue perfusion (e.g., blood flow in the tissue). The voltage across the thermistor (an electrically resistive thermistor bead which is heated in an active mode and unheated in a sense mode) provides a parameter from which a determination of the effective thermal conductivity is made. A data processor 75 of the system separates the thermal effect of perfusion from the thermal effect of intrinsic thermal conductivity. The perfusion value is indicative of shock and may then be used to calculate an SOS value for the tissue. The signal $V_h(t)$ from the power source and control circuit 65 is indicative of the power or thermal energy supplied by the control circuit 65 to the thermistor. This value is also a function of the thermal response in the tissue resulting from the application of heat. The signal $V_h(t)$, functionally related to effective thermal conductivity of tissue, is supplied in digital form via a suitable analog-to-digital converter 70 to a data processor 75, such as a digital data processor, that computes the intrinsic thermal conductivity. A reference thermistor (not shown), located on probe 50 and located outside the thermal range or measurement field of thermistor which supplies heat to the tissue, monitors the baseline temperature and provides a signal $V_s(t)$ which adjusts for baseline temperature shifts. That is, the measured signal $V_s(t)$ may be subtracted from any values to obtain a corrected value used to calculate the intrinsic thermal conductivity.

The reference thermistor is often used where baseline temperature shifts are (or are expected to be) substantial enough to interfere with effective monitoring. In stable thermal environments the compensation provided by reference thermistor is not required. In accordance with preferred embodiments, the data processor 75 processes power related signals from the control circuit 65 and any baseline signals from the reference thermistor (if used) and outputs a signal to a display device 80. The outputted signal is indicative of blood flow in the tissue, and, thus represents the state-of-shock of the tissue, e.g., reduced blood flow may be used as an indicator of shock.

In certain embodiments, one or more algorithms are used to calculate the blood flow values. In other embodiments, a blood flow model, which typically is an algorithm embedded in the controller or is an algorithm readable by the data processor from a disk or other magnetic or optical media, is used to process the signals received from the probe.

A thermal property model determines the intrinsic thermal conductivity ($k_o$) as a function of the power supplied to the thermistor (by the signal $V_h(t)$ provided by control circuit 65) and the baseline signal in embodiments where baseline adjustment is required. Using the blood flow algorithm or model, the data processor computes the blood flow value of tissue.

Figure 4:
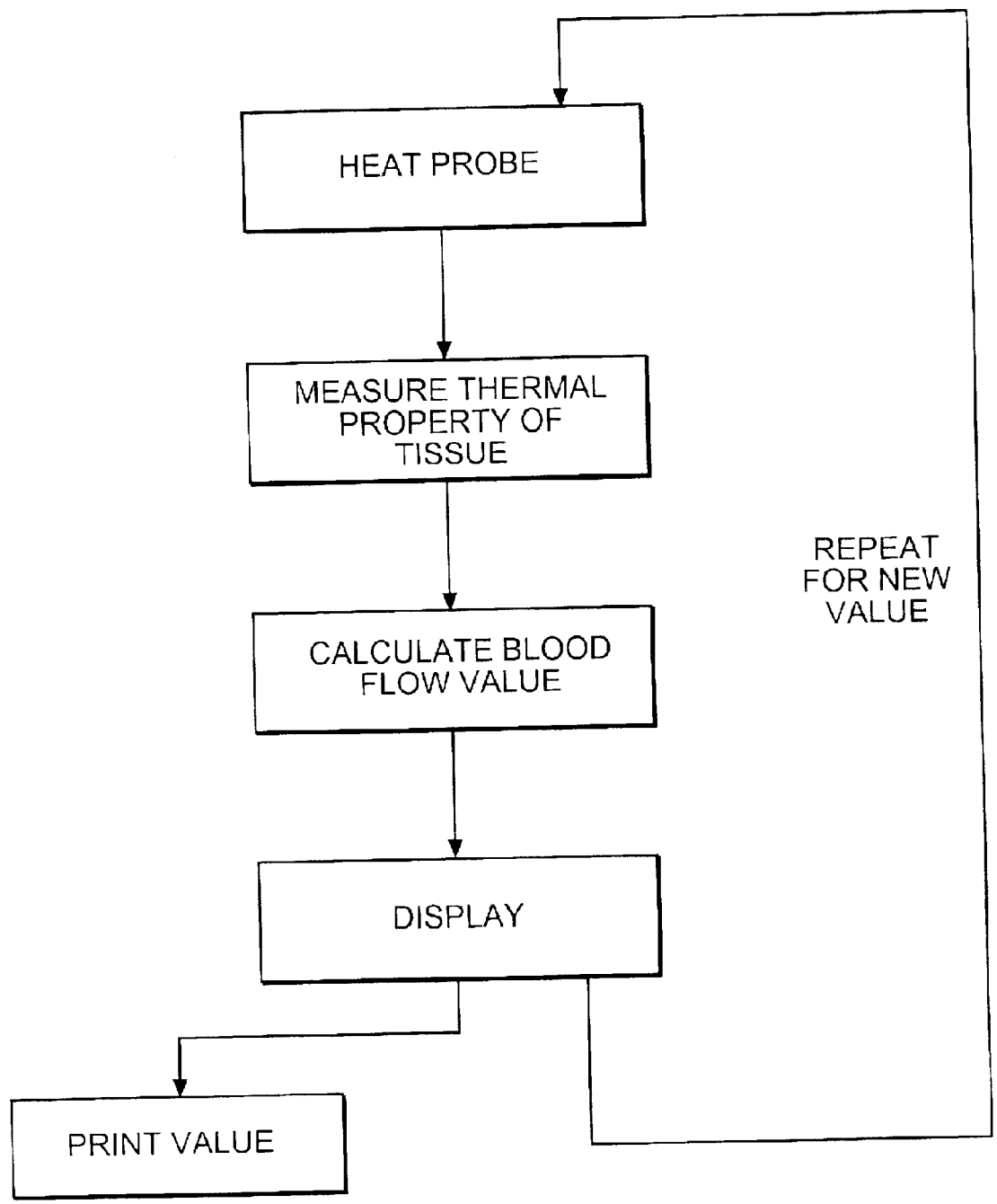
FIG. 4 shows a continuous process for monitoring blood flow values in accordance with a preferred embodiment.

In accordance with preferred embodiments, because the blood flow is reduced during shock, this change is reflected in a corresponding change in the value of a thermal property of tissue such as conductivity and diffusivity. During shock, for example, blood flow will typically decrease in organs and tissues, such as tissue in the inner wall of the rectum. In accordance with preferred embodiments, a measure of at least one of the blood-dependent thermal properties of tissue, for example, thermal conductivity, is made and used to quantify the tissue blood flow (e.g., to quantify shock). Optionally, the blood flow value may be converted to an SOS value for display or printing. A summary of this process is shown FIG. 4.

In accordance with preferred embodiments, a description of thermal property model and mathematics for a method for determining effective thermal conductivity, thermal diffusivity and intrinsic thermal conductivity are described in U.S. Pat. Nos. 4,059,982 and 4,852,027, the entire disclosures of each of which are hereby incorporated herein by reference. As taught there, various heating protocols can be used to heat the thermistor. The thermistor can be heated to a constant or predetermined temperature or thermistor temperature can be measured during heating at a constant or predetermined power or other heating protocols can be used.

In all protocols, procedures using the same principles are used to analyze data. Power used to heat the thermistor and the temperature rise of the thermistor are functional inputs to the calculation of tissue blood flow and, in calculating blood flow, one of the values is predetermined.

Figure 5A:
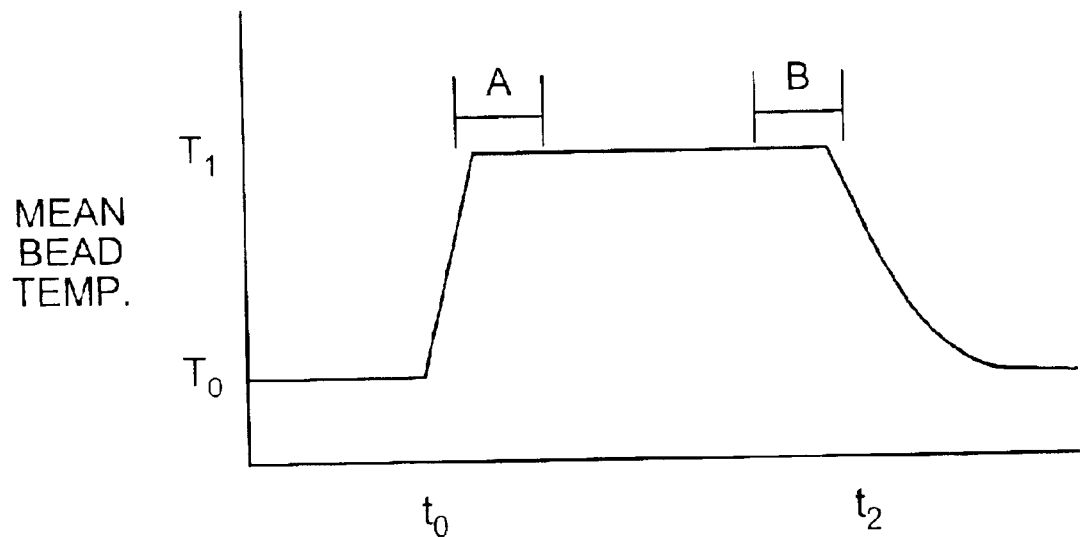
FIG. 5 is a graphical representation of mean bead temperature and of heating power.
Figure 5B:
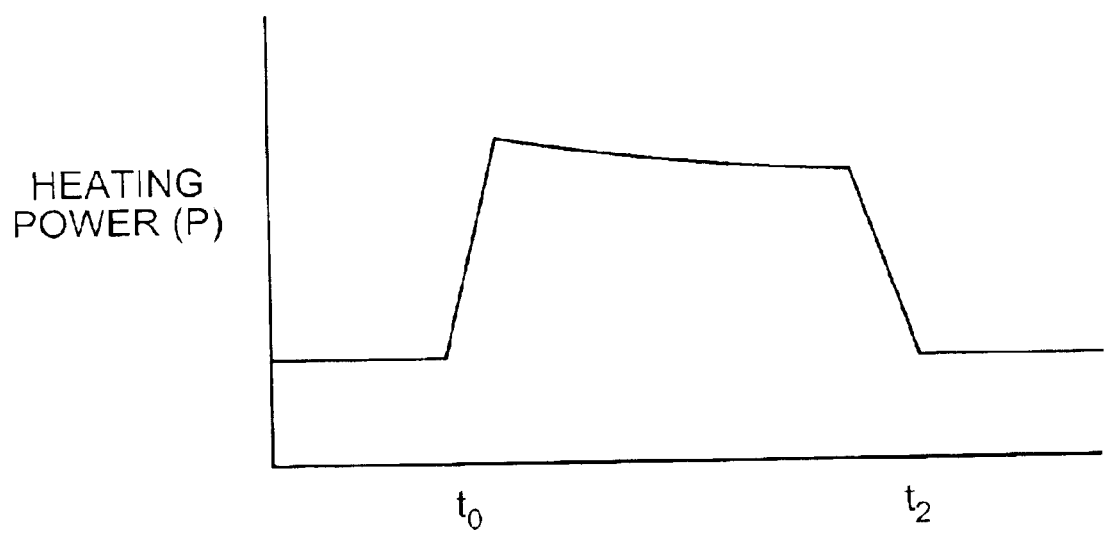

In accordance with preferred embodiments, FIG. 5 is a graphical representation of the mean bead temperature $T_b$ and of the heating power P, both as functions of time. In the particular procedure illustrated, power P is applied in a manner such that the thermistor bead temperature $T_0$ rapidly rises to a selected level $T_1$ at time to $t_0$ heat a volume of tissue and is maintained at that level for a selected time period (until time $t_2$, for example) at which time the power is reduced to zero (shut-off) and the temperature falls to baseline temperature $T_0$ in a general manner as shown completing one energizing and deenergizing cycle. Approximation algorithms, as discussed below, can be used with data derived from measurements taken at different times during the overall heating/cooling cycle as, for example, early in the heating portion thereof at the time range or time window, illustrated by "A" in FIG. 5 and later in the heating portion at "B". Data taken during time window "A" are dominated by tissue conduction (i.e., conductivity) and the effects of the blood flow (perfusion) in the tissue are relatively low. That is, data taken during window "A" is approximately equal to the thermal conductivity of the tissue. Data taken during the time window "B", occurring later in time as heating continues, are influenced to a greater extent by perfusion, (i.e., the effects of blood flow in the tissue are much greater than at time window "A".) That is data taken during window "B" is dominated by the blood flow value.

Figure 6:
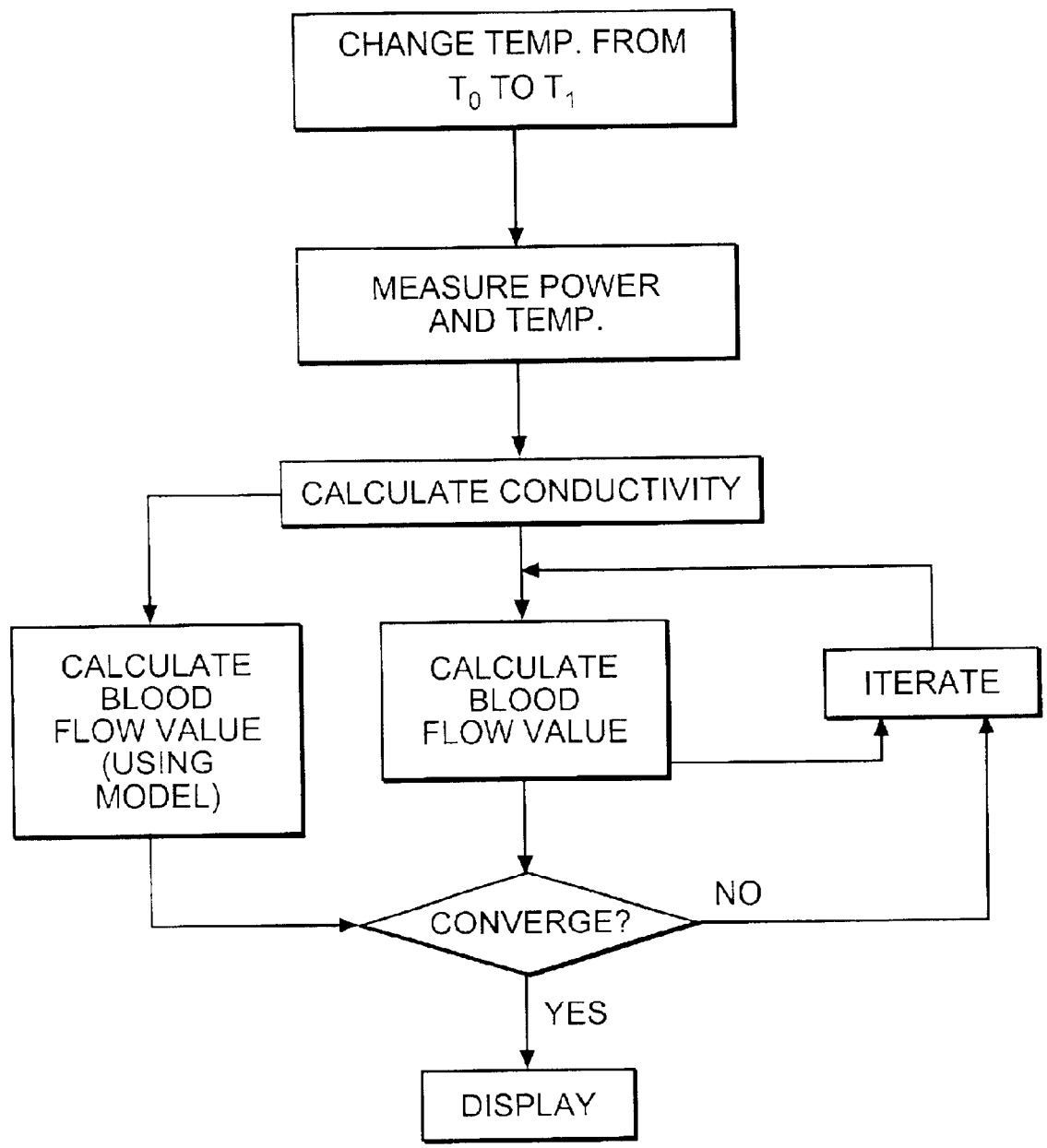
FIG. 6 is an algorithm used to calculate blood flow values in accordance with preferred embodiments.

An exemplary data analysis algorithm usable at time windows "A" and "B" is illustrated by the flow chart of FIG. 6. As stated, the effects of the blood flow of the medium during the time window "B" are greater than during time window "A." Calculations with respect to time windows "A" and "B" can be made as follows:

(a) increase the temperature of the thermistor from a baseline temperature $T_0$ to a first temperature $T_1$ to initiate a thermal cycle while controlling in a predetermined manner either the temperature or the power required to effect the temperature change;

(b) allow the temperature to return to the baseline temperature $T_0$ at the end of a heating cycle;

(c) measure temperature and power;

(d) calculate a value of the intrinsic thermal conductivity and/or diffusivity during time window "A", assuming a value of zero for perfusion;

(e) calculate a tissue blood flow using the values(s) from step (d); and (f) display the calculated SOS blood flow value (or SOS value).

Alternately, if a smaller margin of error is required than that obtained above in step (e), iterative calculations are performed following step (d) as follows:

(g) using the calculated values of intrinsic thermal conductivity and/or diffusivity from step (d) above, calculate a value for perfusion during time window "B";

(h) using the calculations of the thermal conductivity and/or diffusivity as calculated during time window "A" and the perfusion value as calculated during time window "B" recalculate the thermal conductivity and/or diffusivity during time window "A";

(i) using such recalculations for intrinsic thermal conductivity and/or diffusivity, recalculate the value for perfusion during time window "B";

(j) using such recalculated perfusion and recalculated values for intrinsic thermal conductivity and/or diffusivity recalculate again thermal conductivity and/or diffusivity, repeat steps (g) through (i) until convergence to substantially non-changing thermal conductivity and/or diffusivity value(s) is achieved;

(k) calculate to quantify tissue blood flow value using the converged values(s); and (l) display the calculated tissue blood flow value (or SOS value).

Figure 7:
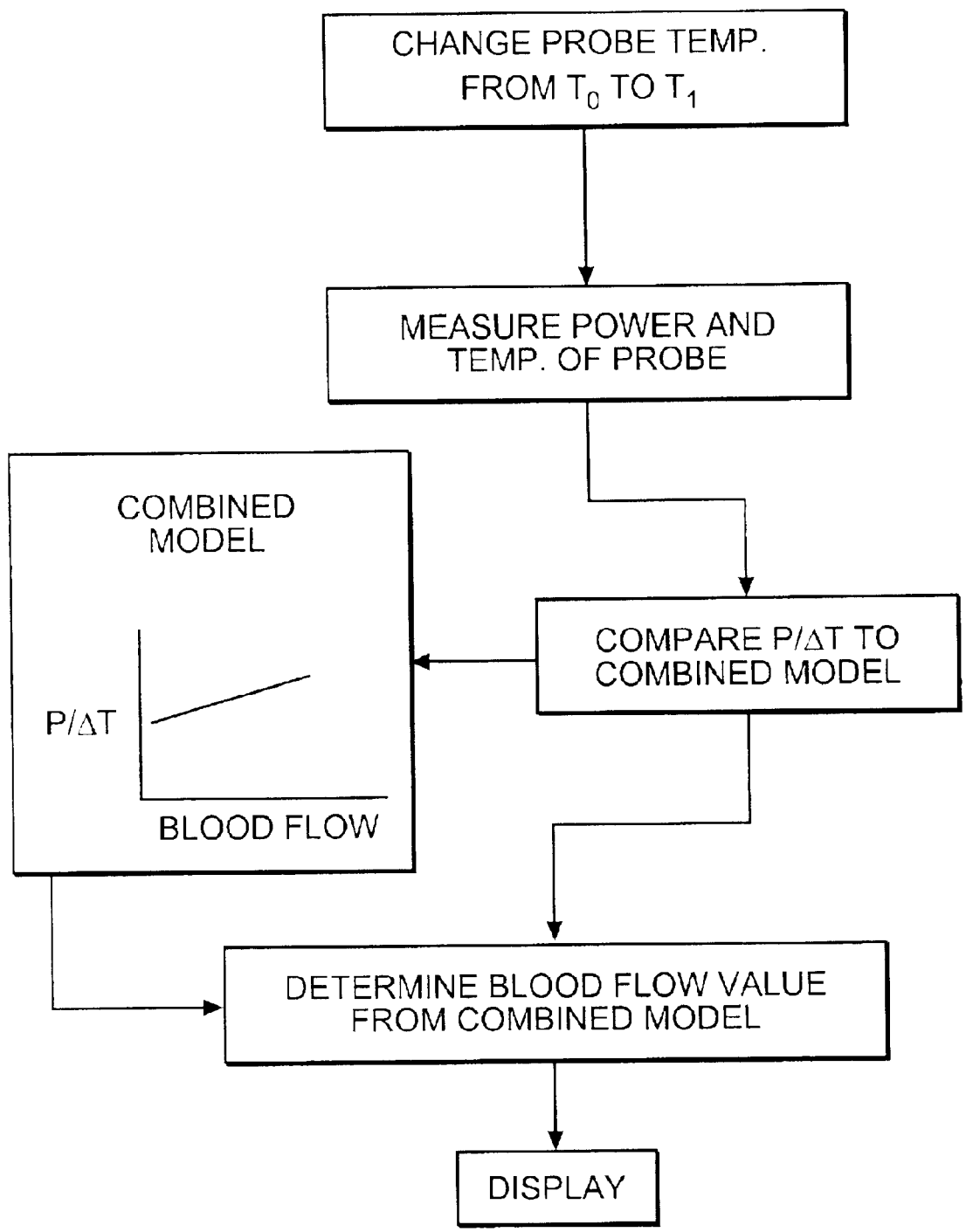
FIG. 7 is a process for calculating blood flow values in accordance with preferred embodiments.

In accordance with preferred embodiments, FIG. 7 illustrates a further embodiment in which blood flow is determined from various parameters affected by the conductivity or other thermal property of tissue without a calculation of the thermal property value. Temperature, power and a model that relates them both (P/dT) to tissue blood flow are used in the direct calculation of blood flow. The model may be empirically or theoretically based. The steps are typically as follows:

(a) change the temperature of the thermistor from a baseline temperature $T_0$ to a first temperature $T_1$ to initiate a thermal cycle while controlling either the temperature or the power required to effect the temperature change;

(b) allow the temperature to relax from the second temperature to a final temperature ($T_f$) at the end of a heating cycle;

(c) measure temperature (T) and power (P);

(d) determine the ratio of power to the change in temperature (P/dT);

(e) using the combined model determine a blood flow value corresponding to the value of P/dT resulting from step (d); and (f) display the blood flow value (or SOS value).

Figure 8A:
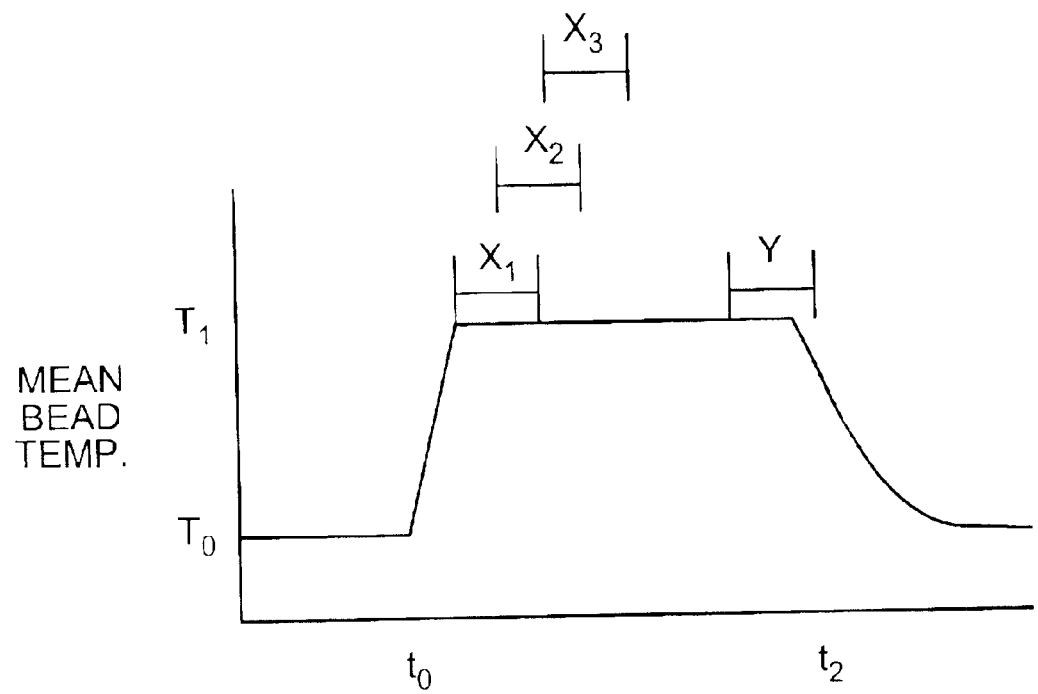
FIGS. 8a and 8b are embodiments useful in calculating blood flow values.
Figure 8B:
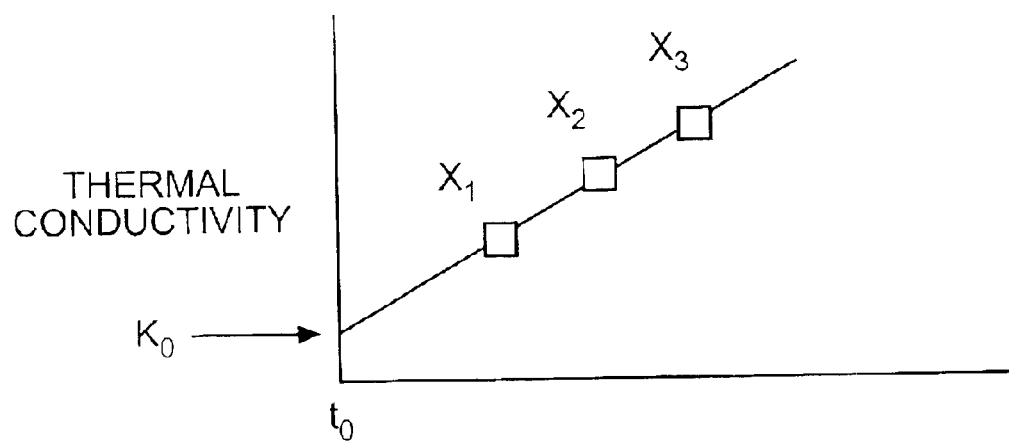

In accordance with preferred embodiments, another exemplary alternative algorithm may be used to calculate thermal conductivity (or thermal diffusivity) values by data extrapolation. The algorithm illustrated by FIG. 8 comprises the following steps:

(a) calculate a plurality of effective thermal conductivity (and/or thermal diffusivity) values during a plurality of time windows $X_i$ where $X_i$ is $X_1, X_2, X_3 \ldots X_n$, where n is the total number of windows (see FIG. 8a), with an assumed perfusion value of zero;

(b) extrapolate the thermal conductivity values obtained in step (a), above to time $t_o$, i.e., to the instant of time at which heating begins, to obtain values for intrinsic thermal conductivity (See FIG. 8b);

(c) calculate a tissue blood flow value using the values(s) from step (b); and (d) display the calculated tissue blood flow value (or SOS value).

A value for tissue blood flow with no substantial margin of error can be obtained by continuing the calculation process according to the following steps:

(e) use extrapolated values of intrinsic thermal conductivity or diffusivity from step (b) above to calculate the perfusion at a selected time during which a perfusion effect occurs, e.g., time window "Y" (see FIG. 8a);

(f) recalculate the intrinsic thermal conductivity or diffusivity at said plurality of time windows $X_i$ using the calculated perfusion value for the selected time window "Y";

(g) extrapolate the thermal conductivity or diffusivity values obtained in step (f) to time $t_o$; and (h) repeat steps (f) and (g) until intrinsic thermal conductivity or thermal diffusivity values converge to substantially non-changing values;

(i) calculate tissue blood flow using the values(s) from step (h); and (j) display the calculated tissue blood flow value (or SOS value).

The extrapolated values typically represent the nonperfused, intrinsic thermal conductivity ($k_o$) value. That is, the thermal conductivity in the absence of a perturbing signal from the probe. For illustrative purposes only and without limitation, an example of this novel technology is described below.

In preferred embodiments, a Qflow 400 Instrument (Thermal Technologies Inc., Cambridge, Mass.) may be used. This instrument requires a host computer for operation to store and display the data. For routine clinical use, however, certain embodiments of the instrument are adapted to function as a stand-alone system, without the need for an external computer. The instrument optionally comprises a display screen and a strip-chart recorder. In certain embodiments, the instrument comprises an embedded x86 or RISC architecture microprocessor.

Figure 9:
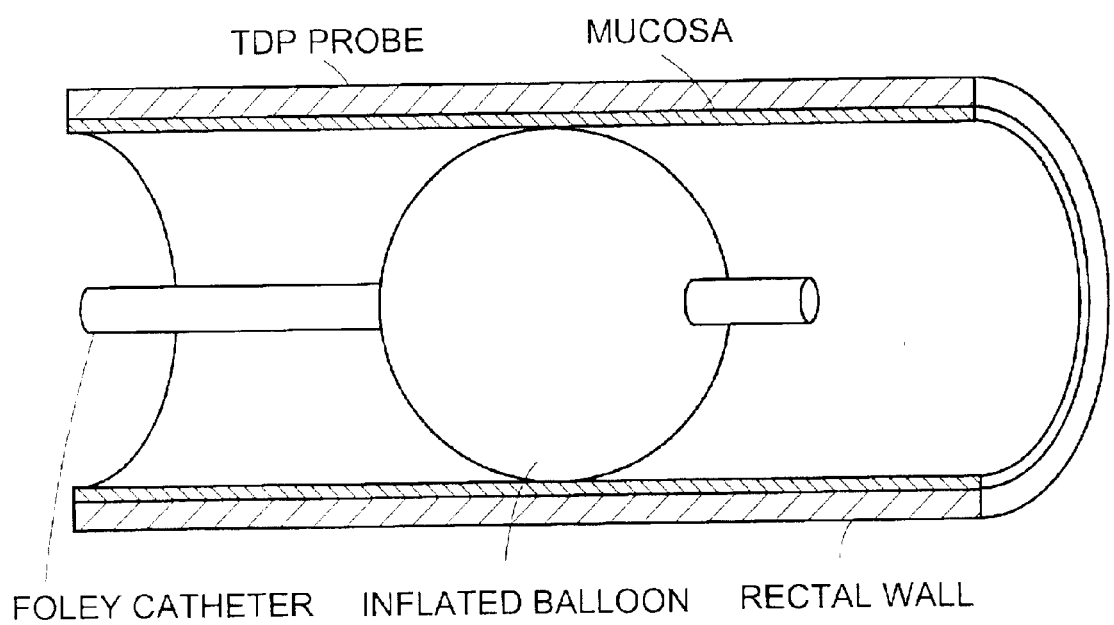
FIG. 9 is a probe suitable for use in a system for monitoring shock.

In accordance with preferred embodiments, a stand-alone perfusion monitor is used to measure rectal wall perfusion. A probe, such as the probe shown in FIG. 9, is inserted into the rectum. The probe typically is based on a standard 18-gauge Foley catheter and has a perfusion sensor epoxied at the equator of the balloon. This probe is inserted into contact with tissue, such as the inner wall of the rectum and the blood flow in the tissue is monitored. Other probes are suitable for use including but not limited to intraluminal probes. FIG. 9 shows a schematic of a possible intraluminal probe. The intraluminal probe design utilizes a standard 18-gauge Foley catheter with a 30 cc balloon. The perfusion sensor is epoxied at the equator of the balloon, and the proximal part of the catheter tubing is attached along the shaft of the Foley catheter. When in use, the balloon is inflated to an optimal inflation pressure such that good thermal contact between the sensor and the mucosa is maintained and yet the pressure is not so great as to cause capillary collapse in the underlying vasculature.

During shock, blood flow to the peripheral tissues is sacrificed, for the sake of the heart and the brain. Diminished rectal wall blood flow will correlate with diminished splanchnic blood flow. The rectal wall is an easily accessible tissue in which to make perfusion measurements for shock monitoring and to guide resuscitation therapy. The response of rectal wall blood flow in a shock model is a proxy for the blood flow in the small bowel, which is an indicator of shock.

To make measurements with a self-heating thermistor, a constant temperature is maintained throughout a measurement sequence. A single host PC computer controls the thermistor temperature and records and displays the results. The heat thermistor is excited to a constant temperature slightly above the tissue baseline (selectable at about 2° C. with a 0.001° C. stability). Data on the power dissipated in the heat thermistor is collected and the baseline tissue temperature is constantly monitored using a passive thermistor (e.g., a reference thermistor) placed outside the heated field. Control of the data collection, the A/D conversion, and the communication with the host computer can be performed using an embedded microprocessor (Intel 8052 family).

Example of Validation Studies

Correlation of Rectal Wall Blood and State-of-Shock

A Qflow 400 Instrument (Thermal Technologies Inc., Cambridge, Mass.) is used and modified as a multi-channel perfusion monitor. This instrument requires a host computer for operation to store and display the data. For routine clinical use, however, certain embodiments of the instrument are adapted to function as a stand-alone system, without the need for an external computer. The instrument optionally comprises a display screen and a strip-chart recorder. In certain embodiments, the instrument comprises an embedded x86 or RISC architecture microprocessor.

In accordance with preferred embodiments, in vivo studies are performed to determine the extent to which rectal wall blood flow correlates with gut flow during conditions of shock and resuscitation. The true value of this perfusion monitoring technique lies in the ability to improve recovery outcome from a standard shock insult. In accordance with additional embodiments, a stand-alone perfusion monitor is used to measure rectal wall perfusion during shock/resuscitation models. The acute survival of animals whose resuscitation is guided by rectal wall perfusion, is compared to the survival of a control group whose resuscitation is guided by standard monitored parameters.

In accordance with preferred embodiments, a probe, such as the probe shown in FIG. 9, is inserted into the inner wall of the rectum. The probe typically is based on a standard 18-gauge Foley catheter and has a perfusion sensor epoxied at the equator of the balloon. This probe is inserted into contact with tissue, such as the inner wall of the rectum and the blood flow in the tissue is monitored. Other probes are suitable for use including but not limited to intraluminal probes. FIG. 9 shows a schematic of a possible intraluminal probe. The intraluminal probe design utilizes a standard 18-gauge Foley catheter with a 30 cc balloon. The perfusion sensor is epoxied at the equator of the balloon, and the proximal part of the catheter tubing is attached along the shaft of the Foley catheter. When in use, the balloon is inflated to an optimal inflation pressure such that good thermal contact between the sensor and the mucosa is maintained and yet the pressure is not so great as to cause capillary collapse in the underlying vasculature. The optimum contact pressure is determined through routine experimentation, such as the experimentation previously performed for determining the optimal contact pressure for probes attached to the skin.

Figure 10:
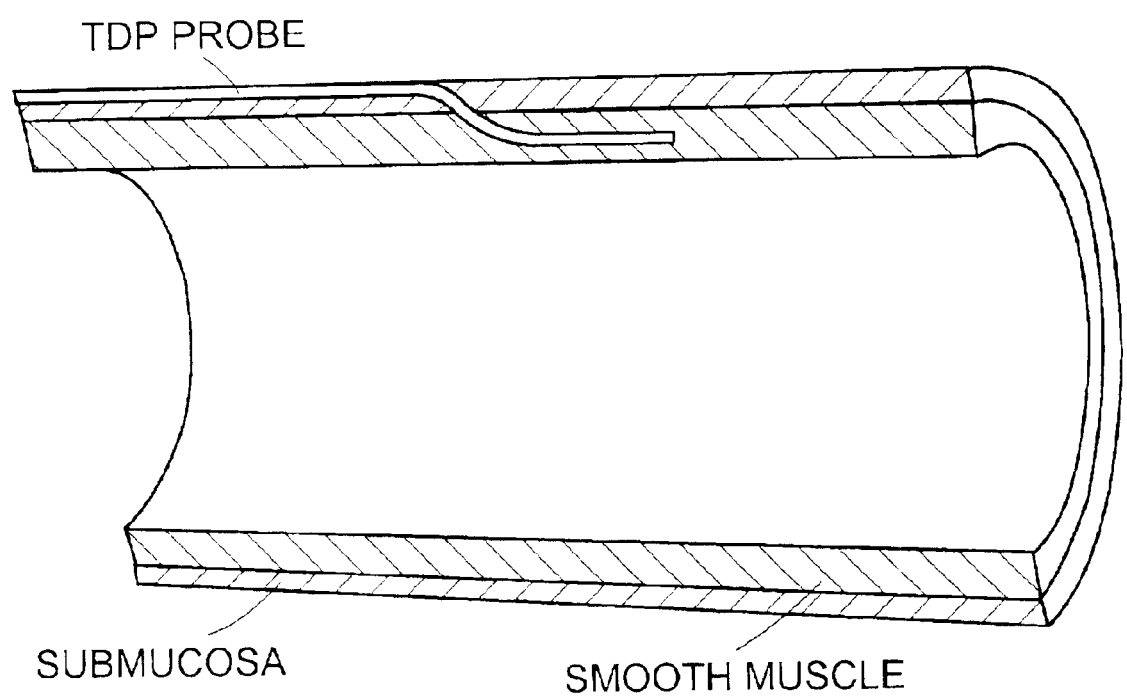
FIG. 10 is a first embodiment for placement of a probe.
Figure 11:
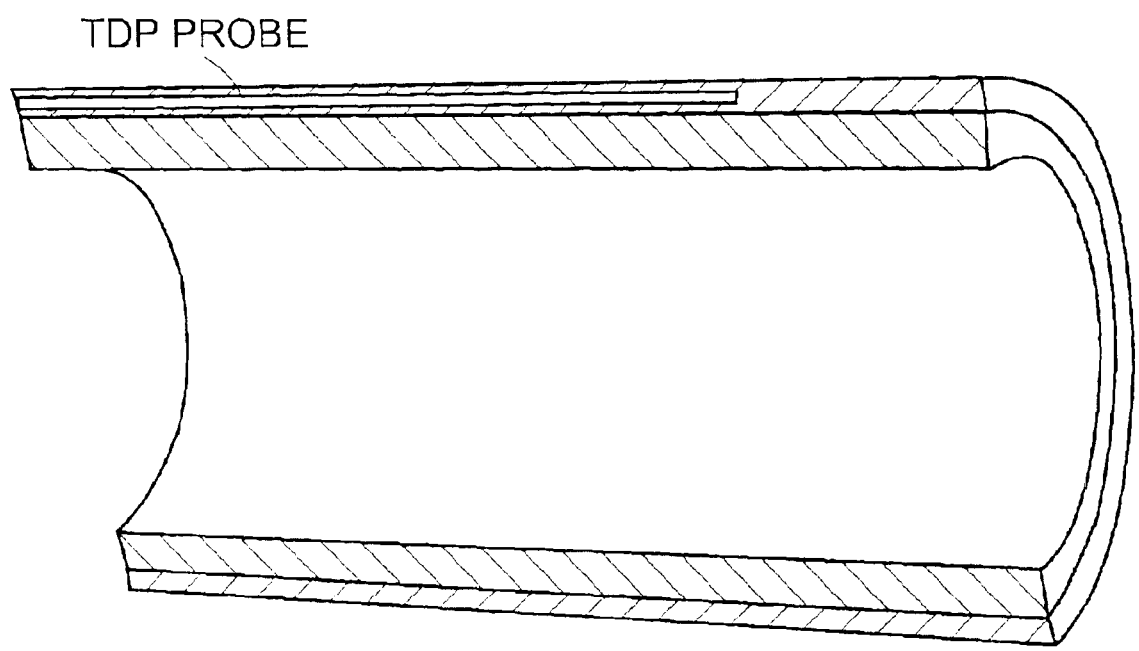
FIG. 11 is a second embodiment for placement of a probe.

In accordance with preferred embodiments, to measure the blood flow in the small bowel, a probe is intraoperatively placed in the small bowel (see FIGS. 10 and 11). Such placement allows for the simultaneous measurement of blood flow in the gut and in the rectum. Typically, the probe is be tunneled about 1.5 cm into the submucosa of the small bowel and the probe is sutured to the smooth muscle as it enters the tissue (see FIG. 10). In alternative embodiments the probe is placed on the surface of the small bowel (see FIG. 11).

By placement of the probe on the small bowel surface, the measurement of blood flow in the small bowel is directly analogous to the intraluminal measurement of rectal wall flow in which the perfusion sensor is also applied to the tissue surface. For the surface application, the probe may be directly sutured to the intestine surface or is held in place using a special holder designed to apply the probe to the outside of the small bowel wall. As with the rectal probe, the intestine probe holder is designed to apply an optimal amount of pressure to the sensor and the intestine wall to maintain good thermal contact and not disturb the blood flow or the normal organ function.

During shock, blood flow to the peripheral tissues is sacrificed, for the sake of the heart and the brain. Therefore, diminished rectal wall blood flow will correlate with diminished splanchnic blood flow. The rectal wall is an easily accessible tissue in which to make perfusion measurements for shock monitoring and to guide resuscitation therapy. The response of rectal wall blood flow in a shock model is studied by comparing the blood flow in the rectal wall with the blood flow in the small bowel. Typically, 2-channel perfusion measurements are taken such that blood flow measurements in the rectal wall and in the small bowel may be recorded simultaneously by a single instrument. Thus, the purpose of the small bowel probe is to provide the independent assessment of gut flow for correlation with rectal flow to determine the value of rectal flow as a proxy measurement of gut ischemia. It is likely that such a probe and holder would also find application to flow quantification during procedures such as aortic reconstruction and clamping when the gut is at risk for ischemia.

This instrument (hardware, software, and firmware) is used in a porcine hemorrhagic shock model. The rectal wall and small bowel blood flow are correlated with global parameters of shock (heart rate, cardiac index, blood pressure, etc.) as well as local tissue indicators of ischemia ($pO_2$, $pCO_2$, and pH). The extent to which rectal wall perfusion measurements correlate with small bowel perfusion during shock and recovery is determined.

To make simultaneous measures of perfusion at 2 sites, a separate instrument module typically is used for each of the 2 measurement channels. With the perfusion sensor, self-heating of the distal thermistor is continuously maintained throughout a measurement sequence. The instrument module cannot be temporarily disconnected from the sensor in order to measure perfusion at the next sensor. Each measurement channel requires a dedicated module for simultaneous reporting. The multiple modules are under the control of a single host PC computer that controls the channels and record and display the results. Each module excites the heat thermistor to a constant temperature slightly above the tissue baseline (selectable at about 2° C. with a 0.001° C. stability), collects data on the power dissipated in the heat thermistor, and constantly monitors the baseline tissue temperature using a passive thermistor (e.g., a reference thermistor) placed outside the heated field. Control of the data collection, the A/D conversion, and the communication with the host computer are typically performed using an embedded microprocessor (Intel 8052 family). Electrical isolation of the instrument from the wall ground is provided using a UL554 Medical Grade Power Supply and isolation from the computer is achieved with an optically isolated communication port. The instrument meets the patient safety standards defined in IEC-601-1 for Cardiac Floating (type CE) Equipment. The "Patient Risk Sink Current" (Zero-Fault Leakage) for the QFlow 400 is 6 $\mu$A versus a maximum of 10 $\mu$A for the standard and the "Patient Risk Source Current" (Single-Fault Leakage) is 6.3 $\mu$A versus a maximum of 10 $\mu$A for the standard. The instrument also passes the "Dielectric Strength" test (break-down voltage) to 3000 V.

The QFlow 400 boards are adapted to communicate serially with the host computer through the RS-485 protocol. The RS-485 protocol is designed so multiple receivers and drivers can share the same physical line—like a computer bus. RS-485 communicates with a differential voltage signal so rates as high as 10 Megabits/second can be transmitted and the cable length may be as long as 1200 meters (though both are not typically possible at the same time).

In the QFlow 400, RS-232 serial communication is mediated by the MAX232 chip (Maxim Technologies, Inc., Sunnyvale, Calif.). In the multi-module, a new chip-set (MAX487, Maxim) is be installed to permit the RS-485 communication. In alternative embodiments, wireless communication between a transmitter in communication with the probe and a receiver in communication with the instrument is used.

Each QFlow 400 single channel Perfusion Monitor contains an embedded microprocessor (DS87C520 from Dallas Semiconductor—Intel 8052 family) that collects data from the A/D converters, calibrates the amplifiers, and controls communication with the host PC. The machine code firmware that runs the microprocessor is created with compiled basic (BC15 Basic Compiler from Systronix). The machine code is then downloaded into a 16 KB on-board EPROM (Electrically Programmable Read Only Memory). In a multi-channel instrument, the firmware is modified with the ability to identify the intended recipient of a command from the host PC. The firmware checks and verifies the address tag to determine if it should execute that command. Similarly, when data are sent from the module to the host computer, the outgoing data is tagged with the module identifier. Also, since the serial line is shared among all modules, the module has to check if a status line is ready, unsets the status line, and then sends the data.

To perform the measurement of monitoring rectal blood flow a porcine hemorrhagic shock model is used (Six Yorkshire pigs, 30 kg, are used in this study). Each pig is pre-anesthetized with ketamine/xylazine (2.2/0.21 mg/kg) and sulfate atropine (0.05 mg/kg) and intubated. A gastric tonometer is placed in the stomach and pHi is recorded every 30 minutes. Ventilation using isofluorane (1–1.5% isofluorane, 4–6 l/mn), ear vein cannulation, and starting of a saline drip is performed. The bowel of each pig is prepared using one or more enemas. A carotid artery cut-down for blood-pressure monitoring and arterial blood gas withdrawal is performed. Femoral artery and venous cut-down, for hemorrhage and venous blood gas measurements, are performed. Cannulation of the jugular vein and insertion of a Swan-Ganz catheter for cardiac output measurements is performed. A laparatomy is performed and a catheter is placed in the hepatic vein for blood gas measurements. Insert one or more Diametrics pH, $pO_2$, $pCO_2$ and temperature probes into the small bowel wall (ileum). Insert one or more Diametrics pH, $pO_2$, $pCO_2$ and temperature probes into the rectum. Insert one or more thermal diffusion probes (TDP) in the small bowel wall (ileum). Insert one or more TDPs into the rectum (10 cm from anus) against the wall. Continuous monitoring begins after insertion of all probes. The arterial and venous blood gases are recorded every 30 minutes. Animals are allowed to stabilize for 30 minutes prior to introducing any signal into the probes.

To induce shock, blood is withdrawn in 50 ml aliquots over 15 minutes resulting in lowering of systolic blood pressure to 45 mm Hg. This state-of-shock is maintained for 60 minutes. ABG and cardiac output is recorded. Animals are resuscitated with blood and saline to restore mean arterial blood pressure (MAP) to baseline. A MAP>60 mm Hg is maintained and animal recovery is monitored for 120 minutes.

Figure 12:
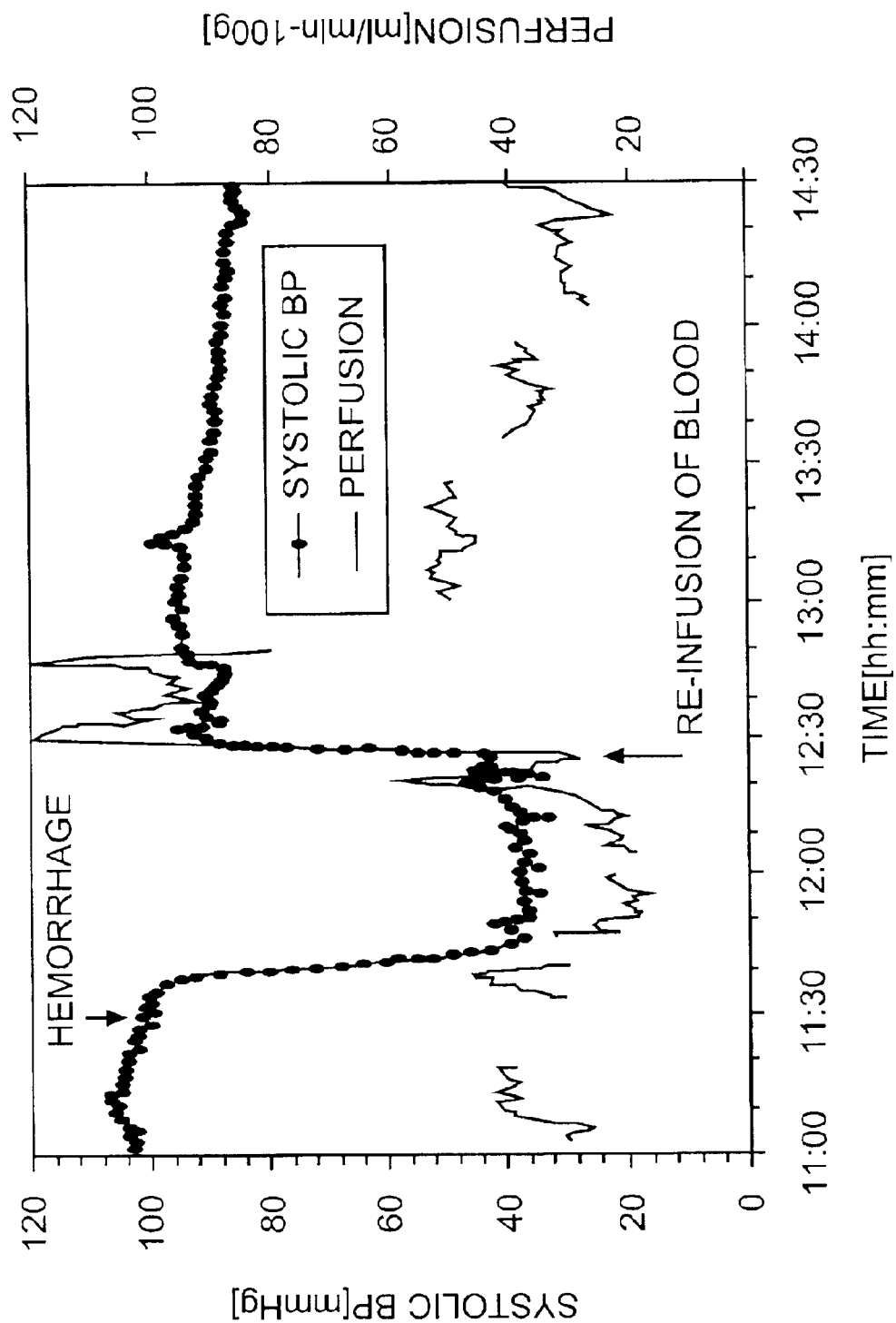
FIG. 12 is a graphical representation of the blood flow response for a porcine shock model.

FIG. 12 shows liver perfusion and systolic blood pressure during hemorrhagic shock in a first porcine experiment. Hemorrhage began at 11:30 and shock was maintained until 12:25 at which time the blood was re-infused. A baseline liver perfusion of 40 ml/min-100 g was measured which declined by about half to 20 ml/min-100 g during shock. After re-infusion of blood, hyperemia was observed with the liver perfusion transiently increasing to 120 ml/min-100 g and later steadily declining to about 30 ml/min-100 g. The gaps that appear in the perfusion data correspond to the instances of in situ calibration when data are not available, in this case once every 30 minutes. The onset of shock greatly reduced blood flow to the gut; perfusion in the liver dropped to about half its baseline value. The hyperemia seen upon re-infusion is also expected because of the oxygen debt that built up in the liver tissue during the time of shock and reduced liver perfusion.

Although the present invention has been described above in terms of specific embodiments, it is anticipated that other uses, alterations and modifications thereof will become apparent to those skilled in the art given the benefit of this disclosure. It is intended that the following claims be read as covering such alterations and modifications as fall within the true spirit and scope of the invention.

What is claimed is:

1. A system for monitoring shock comprising:
    means for supplying heat to tissue in which blood flow typically decreases during shock;
    means for cyclically energizing and deenergizing said heat supplying means;
    means for sensing in the tissue a thermal response functionally related to the perfusion of blood in the tissue during said energizing and deenergizing cycles; and
    means for calculating a value indicative of shock as a function of thermal responses sensed over more than one energizing and deenergizing cycle.

2. The system of claim 1, wherein the means for supplying heat to tissue comprises a thermistor.

3. The system of claim 1, wherein the sensor comprises a thermal diffusion probe.

4. The system of claim 1, wherein the sensor comprises an intraluminal probe.

5. A shock monitor comprising:
    a thermistor for thermal contact with tissue at a site where blood flow typically decreases during shock;
    means for electrically energizing and deenergizing said thermistor to cyclically elevate the temperature of said thermistor above the baseline temperature of tissue at said site;
    means for producing over several temperature cycles an electrical signal the value of which is functionally related to the electrical energy supplied to said thermistor and the rate at which heat from said thermistor is transferred in said tissue; and
    means for producing a signal indicative of shock as a function of said electrical signal.

6. A shock monitor comprising:
    thermistor means for thermally contacting living tissue at a site on the inner wall of the rectum;
    means for electrically energizing and deenergizing said thermistor means cyclically to cause the temperature of said tissue to rise and fall cyclically;
    means for producing a signal functionally related to the power used to energize said thermistor during each energizing and deenergizing cycle;
    means responsive to the temperature change in said tissue and the power related signal from said producing means for producing a signal during each energizing and deenergizing cycle as a function of perfusion in said tissue; and
    means for computing a value for blood flow in said tissue indicative of shock during each energizing and deenergizing cycle as a function of the perfusion related signal.

7. The shock monitor of claim 6, wherein the means for computing a value comprises a microprocessor.

8. The shock monitor of claim 6, wherein the means for computing a value comprises an embedded microdevice.

9. A system for producing a signal indicative of shock comprising:
    a thermistor for contacting the inner wall of the rectum to establish thermal contact with tissue at a site in the inner wall of the rectum;
    control means for electrically energizing and deenergizing said thermistor cyclically to cause the temperature of said thermistor to cyclically rise and fall, the rate of temperature rise in an initial time period within each energizing and deenergizing cycle being substantially a function of the intrinsic thermal conductivity of tissue in thermal contact with said thermistor;

means for producing a signal functionally related to the power used to energize said thermistor during each energizing and deenergizing cycle; and iterative calculating means for:

calculating intrinsic thermal conductivity in the initial time interval during each energizing and deenergizing cycle as a function of the temperature rise in the initial time interval and the power related signal produced by said producing means;

calculating perfusion in a subsequent time interval during each energizing and deenergizing cycle as a function of the calculated value of intrinsic thermal conductivity;

recalculating intrinsic thermal conductivity in the first time interval using the calculated value of perfusion;

recalculating perfusion in the subsequent time interval using the recalculated value of intrinsic thermal conductivity; and recalculating values for intrinsic thermal conductivity and perfusion, in alternating fashion, until the recalculated values of perfusion converge to a substantially unchanging value, using in each recalculation of perfusion the previously recalculated value of intrinsic thermal conductivity and in each recalculation of intrinsic thermal conductivity the previously recalculated value of perfusion.

10. A method of monitoring shock in a living subject comprising the steps of:

supplying heat to tissue in the inner wall of the rectum so as to cause the temperature of the tissue to cyclically rise and fall;

sensing in the tissue a thermal response functionally related to the perfusion of blood in the tissue over several temperature cycles; and calculating a blood flow value indicative of shock as a function said thermal response over more than one temperature cycle.

11. The method of claim 10, wherein the heat is supplied using a thermistor.

12. The method of claim 10, wherein the blood flow value is calculated by comparing the thermal response with a table of thermal response values.

13. A method of monitoring shock comprising the steps of:

contacting tissue in which blood flow typically decreases during shock with electrically energizable thermistor means to establish a heat transfer path between said thermistor means and said tissue;

energizing and deenergizing said thermistor means to cyclically elevate the temperature of said thermistor means above the baseline temperature of said tissue;

sensing the thermal response in said tissue to the application of heat from said thermistor means over several temperature cycles; and calculating a blood flow value indicative of shock as a function of the thermal response in said tissue sensed in said sensing step over more than one temperature cycle.

14. The method of claim 13, wherein the blood flow value is calculated by comparing the thermal response with a table of thermal response values.

15. A method of monitoring shock comprising the steps of:

contacting the inner wall of the rectum with electrically energizable thermistor means to establish a heat transfer path between said thermistor means and tissue at a site along the inner wall of the rectum;

energizing said thermistor means to elevate the temperature of said thermistor means above the baseline temperature of said tissue;

sensing the thermal response in said tissue to the application of heat from said thermistor means;

calculating intrinsic thermal conductivity in a first time interval during said energizing step;

calculating perfusion in a subsequent time interval during said energizing step using the calculated value of intrinsic thermal conductivity;

recalculating values for intrinsic thermal conductivity and perfusion in alternating fashion, until the recalculated values of perfusion converge to a substantially unchanging value, using in each recalculation of perfusion the previously calculated value of intrinsic thermal conductivity and in each recalculation of intrinsic thermal conductivity the previously calculated value of perfusion; and calculating a blood flow value indicative of shock as a function of the converged value of perfusion.

16. A method of monitoring shock comprising the steps of:

contacting the inner wall of the rectum with a thermistor to establish a thermal transfer path with tissue at a site in the inner wall of the rectum;

electrically energizing and deenergizing said thermistor cyclically to cause the temperature of tissue in thermal contact with said thermistor to cyclically rise and fall, the rate of temperature rise in an initial time period within each energizing and deenergizing cycle being substantially a function of the intrinsic thermal conductivity of tissue in thermal contact with said thermistor;

producing a signal functionally related to the power used to energize said thermistor during each energizing and deenergizing cycle;

calculating intrinsic thermal conductivity of tissue at said site in an initial time interval during each energizing and deenergizing cycle as a function of the temperature rise and said power related signal in the energizing and deenergizing cycle;

calculating perfusion in a subsequent time interval during each energizing and deenergizing cycle as a function of the calculated value of intrinsic thermal conductivity;

recalculating intrinsic thermal conductivity in said first time interval using the calculated value of perfusion;

recalculating perfusion in said subsequent time interval using the recalculated value of intrinsic thermal conductivity;

recalculating values for intrinsic thermal conductivity and perfusion, in alternating fashion, until the recalculated values of perfusion converge to a substantially unchanging value, using in each recalculation of perfusion the previously recalculated value of intrinsic thermal conductivity and in each recalculation of intrinsic thermal conductivity the previously recalculated value of perfusion; and processing said substantially unchanging perfusion value during each energizing and deenergizing cycle to provide a blood flow signal indicative of shock.

17. A system for producing a signal indicative of shock comprising:
  thermistor means for thermally contacting living tissue at a site on the inner wall of the rectum;
  means for electrically energizing and deenergizing said thermistor means cyclically to cause the temperature of said tissue to rise and fall cyclically;
  means for producing a signal functionally related to the power used to energize said thermistor during each energizing and deenergizing cycle; and
  means responsive to the power related signal from said producing means for producing a signal, functionally related to blood flow and indicative of shock, during each energizing and deenergizing cycle as a function of perfusion in said tissue.

18. A system according to claim 17 further comprising a blood flow model wherein said signal indicative of shock is a function of the relationship of said power related signal to said blood flow model.

19. A system according to claim 17 further comprising a model that relates temperature and power to tissue blood flow wherein said signal indicative of shock is a function of the relationship of said power related signal and the change in temperature produced by said energizing and deenergizing means to a blood flow value determined by said model.

20. A system according to claim 19 wherein the relationship of said power related signal and the change in temperature produced by said energizing and deenergizing means is the ratio of said power related signal to said change in temperature.

* * * * *